United States Patent [19]
Burke et al.

[11] Patent Number: 5,299,249
[45] Date of Patent: Mar. 29, 1994

[54] HEAT TRANSFER TECHNIQUES FOR MOVING THERMAL ENERGY FROM HIGH POWER X-RAY TUBES ON ROTATING CT GANTRIES TO A REMOTE LOCATION

[75] Inventors: James E. Burke, Villa Park, Ill.; Anton Z. Zupancic, Kirtland, Ohio; Thomas R. Miller, St. Charles; Patrick P. McNally, Geneva, both of Ill.

[73] Assignee: Picker International, Inc., Highland Heights, Ohio

[21] Appl. No.: 982,477

[22] Filed: Nov. 27, 1992

[51] Int. Cl.⁵ ............................................... H01J 35/10
[52] U.S. Cl. ..................................... 378/15; 378/199; 378/200
[58] Field of Search ............... 378/130, 141, 199, 200, 378/4, 15

[56] References Cited

U.S. PATENT DOCUMENTS

| | | | |
|---|---|---|---|
| 4,644,573 | 2/1987 | Palermo et al. | 378/15 |
| 4,651,338 | 3/1987 | Hahn | 378/199 |
| 4,709,559 | 12/1987 | Dotzauer et al. | 62/499 |
| 4,866,743 | 9/1989 | Kroener | 378/199 |
| 5,012,505 | 4/1991 | Zupancic et al. | 378/130 |

FOREIGN PATENT DOCUMENTS

1527813 10/1978 United Kingdom.
2026812A 2/1990 United Kingdom.

Primary Examiner—David P. Porta
Attorney, Agent, or Firm—Fay, Sharpe, Beall, Fagan, Minnich & McKee

[57] ABSTRACT

A CT scanner has an x-ray tube (B) which is carried by a rotating gantry portion around a patient receiving region (12). A large diameter, annular radiator (30) is connected to the rotating gantry for rotation with the x-ray tube. A cooling oil is circulated around the x-ray tube and through passages (32, 74, 100) of the rotating radiator. An annular stationary member is mounted to a stationary gantry portion (A) of the CT scanner. In the embodiment of FIGS. 2 and 3, the stationary member is an annular tube (36) which substantially surrounds the rotating radiator except for an annular access aperture (38). Spray jets (40) spray the rotating radiator with water which is drained (42), circulated to a remote heat exchange or cooling apparatus (D), and recirculated to the spray nozzles. Baffles (52, 54), gutters (58), lip and baffle arrangements (54, 56), and the like, inhibit the sprayed water from escaping from the tube (36). In the embodiment of FIG. 4, the water is sprayed on a wick member (76). Water evaporates from the wick, cooling the rotating radiator with evaporative cooling. In the embodiments of FIGS. 4 and 5, the rotating and stationary members include interleaved fins vanes (70, 82) between which heat is transferred by air flow. In the embodiment of FIG. 6, a layer of water is carried by centrifugal force into the air gap between a horizontal rotating heat transfer surface (102) and a horizontal stationary heat transfer surface (108).

27 Claims, 5 Drawing Sheets

HEAT TRANSFER TECHNIQUES FOR MOVING THERMAL ENERGY FROM HIGH POWER X-RAY TUBES ON ROTATING CT GANTRIES TO A REMOTE LOCATION

BACKGROUND OF THE INVENTION

The present invention relates to the heat transfer arts. It finds particular application in conjunction with the movement of heat energy from the rotating gantry of a CT scanner to the stationary gantry of the same scanner and will be described with particular reference thereto. It is appreciated, however, that the invention will also find application in conjunction with other equipment in which significant amounts of heat are transferred across rotary couplings.

In early rotating gantry CT scanners, the x-ray tube was immersed in an oil bath and the oil was circulate to a radiator that was also mounted on the rotating gantry. Air was circulated through the radiator into the gantry housing and the surrounding room. The air conditioning and cooling system for the room then removed this heat to a remote location. See for example, U.K. Patent No. 1,527,813 or U.K. Patent Application GB 2026812AA.

As x-ray tubes increased in power, the amount of waste heat which needed to be dissipated also increased. A five inch rotating anode x-ray tube operating on a continuous duty cycle generates about 10 kilowatts of heat. However, most CT scanners have a relatively limited duty cycle. That is, during each exposure, the x-ray tube is normally not on for a sufficient duration to saturate the heat absorbing capacity of the hydraulic fluid and surrounding metal structures. The duration between successive exposures, provides sufficient time for this heat to be removed from the rotating gantry at a lower rate. Only about 4–5 watts of heat removal capacity are required. To handle these higher heat transfers, fluid slip rings have been provided between the rotating and stationary gantry portions. See for example, U.S. Pat. No. 4,709,559 in which an evaporator coil is rotated within a sealed fluid slip ring between the rotating and stationary gantry portions and U.S. Pat. No. 5,012,505 in which the oil from the x-ray tube is transferred with fluidic couplings across the rotating and stationary gantry portions. Although these systems possess a relatively high heat transfer capability, there are drawbacks. In particular, a pressurized fluid seal must be maintained to keep the coolant from leaking.

Another disadvantage of these systems is that they place a large amount of drag on the motor system for the rotating gantry. A significant amount of horsepower is lost to the fluid heat transfer mechanism.

For more complete volume imaging, scanners have been proposed in which the gantry rotates continuously. This enables a volume of the patient to be imaged in a relatively short duration. For example, in order to maintain a 1 millimeter resolution, the patient table is advanced at the rate of 1 millimeter per revolution of the x-ray tube. The x-ray tube and gantry rotate at a sufficiently high speed that a volume of the patient several centimeters long is obtained. Of course, in this continuous spiral scanning of a patient volume, the duty cycle of the x-ray tube is increased. That is, the x-ray tube remains on sufficiently long that it becomes necessary to transfer the heat across the gantry at substantially the same rate that it is generated.

In order to enable the x-ray tube to spin more rapidly while maintaining the present exposure rates, a larger, higher powered x-ray tube is demanded. A seven inch diameter rotating anode x-ray tube, the next generation from the five inch anode x-ray tubes, generates about 50 kilowatts of heat. The present invention is concerned with moving the large amounts of heat from continuous rotation scanners and large diameter anode x-ray tubes.

SUMMARY OF THE INVENTION

In accordance with the present invention, hot oil from the x-ray tube of a CT scanner is circulated through an annular rotating radiator means which extends peripherally around the rotating gantry and rotates therewith. The heat is transferred from the rotating radiator to a stationary member that is separated from the radiator by an air region. A working fluid is circulated between the stationary member and a remote heat exchanger that cools the working fluid.

In accordance with one embodiment of the present invention, a rotating radiator means having a high surface area is connected to the rotating gantry for rotation therewith. The rotating radiator portion is surrounded by a tube mounted to the stationary gantry. The tube defines an annular gap therethrough through which supports and defines a fluid conducting passage in which the rotating radiator is received. Water spray nozzles are provided for spraying the rotating radiator with water. The water drips and sprays from the rotating radiator, flows by gravity to a bottom of the tube, and is drained to a remote location. In this manner, a fluid heat transfer is achieved without high pressure fluid seals. Gutters, baffles, coatings, and the like are sufficient to prevent the sprayed water from splashing out the annular access opening.

In accordance with another aspect of the present invention, the rotating gantry portion carries an annular radiator which has a water absorptive layer centrally therealong. A stationary cold water radiator is disposed adjacent the hot water radiator. The stationary cold radiator includes one or more annular gutter regions including a gutter region opposite the porous material. Water jets are provided in the stationary gutter to spray the porous material with water. Heat from the first radiator causes the water to evaporate from the porous material such that the heat of vaporization removes significant heat from the first radiator. Air is passed between the two radiators with hot humid air being withdrawn to remove the hot water vapor laden air and to supply new cool dry air at a sufficient rate that the air does not saturate stopping the evaporation of water from the porous material.

In accordance with another aspect of the present invention, an annular radiator is mounted to the rotating gantry portion. A stationary gutter surrounding the annular radiator is provided on the stationary gantry portion. A stationary cooler ring through which chilled cooling water flows is mounted in close proximity to the rotating annular radiator with the two defining a relatively narrow gap therebetween. During rotation, centrifugal force carries water between the rotating radiator surface and the stationary cooler ring for efficient heat transfer. The gutter is sufficiently high that splashing is prevented during rotation and such that an adequate reservoir is provided to hold all of the water when rotation stops.

In accordance with another aspect of the present invention, an annular radiator is mounted to the rotating gantry portion for rotation therewith. The rotating radiator defines a plurality of alternating annular ribs and valleys. A stationary cooling structure has internal cooling passages for cooling fluid and a plurality of analogous extending rings and valleys. The rotating and stationary ribs and valleys intermesh, defining narrow gaps therebetween. Cold air is pumped between the annular ribs and valleys to transfer heat thereacross. The air flow rate and the number of ribs and valleys is selected to be sufficiently large that discharged air is sufficiently cool that it can be safely discharged into the gantry region and the patient room without causing overheating problems.

One advantage of the present invention is that it requires no seals.

Another advantage of the present invention is that it moves substantial amounts of heat.

Another advantage of the present invention is that it uses chilled water as the working medium to convey heat.

Another advantage of the present invention is that the absence of seals reduces drag on the gantry rotating motor.

Another advantage of the present invention resides in its simplicity. The present invention can be readily used with existing scanners which are retrofit for higher power tubes.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
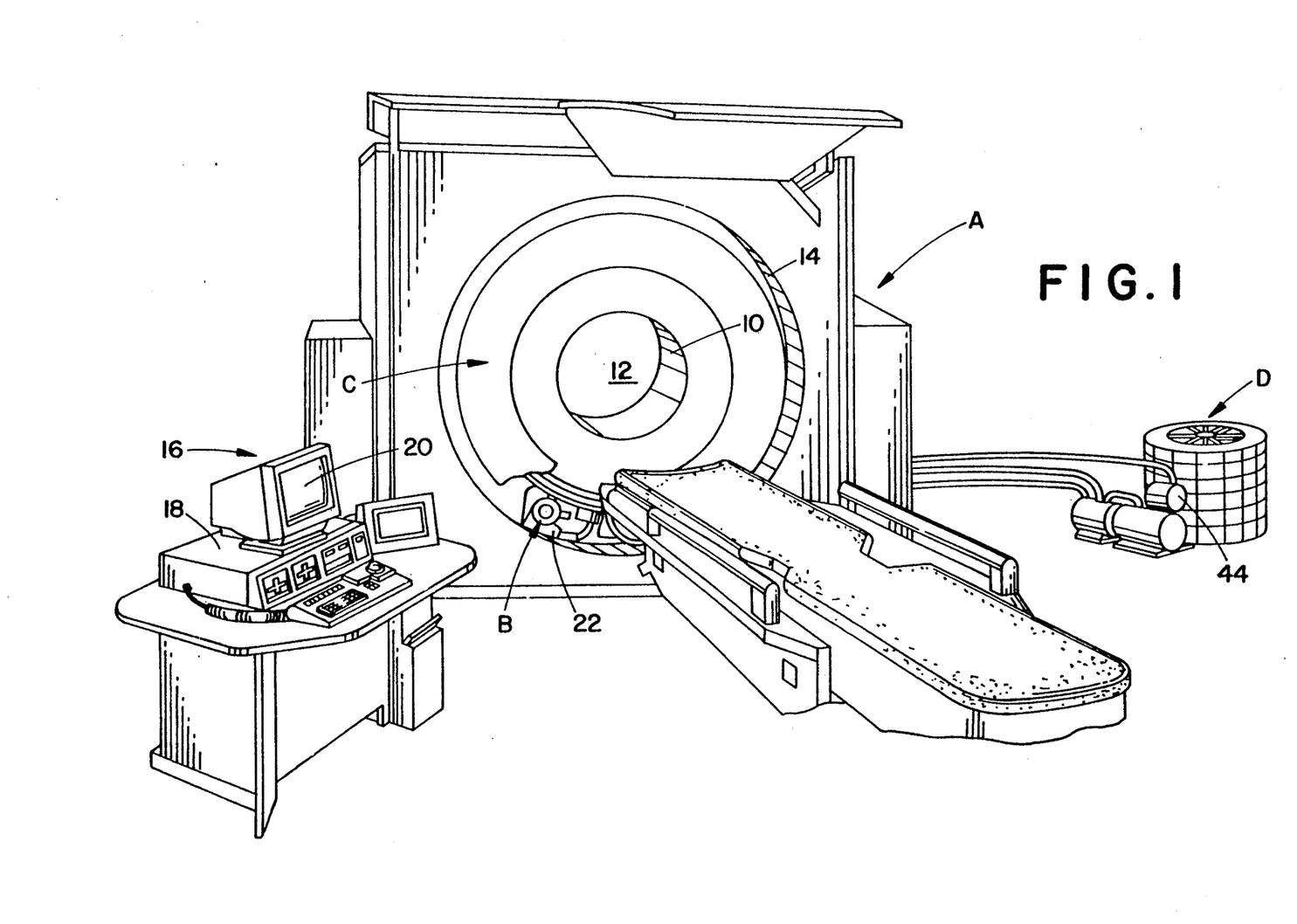
FIG. 1 is a diagrammatic illustration of a CT scanner in accordance with the present invention.

With reference to FIG. 1, a CT scanner includes a floor mounted or stationary gantry A whose position remains fixed during data collection. An x-ray tube B is rotatably mounted on a rotating gantry. An annular heat exchanger C transfers the heat generated during the generation of x-rays by the x-ray tube to the stationary gantry and to a remotely located heat exchanger D.

The stationary gantry A includes a cylinder 10 that defines a patient receiving examination region 12. An array of radiation detectors 14 are disposed concentrically around the patient receiving region. In the illustrated embodiment, the x-ray detectors are mounted on the stationary gantry portion such that an arc segment of the detectors receives radiation from the x-ray tube which has traversed the examination region 12. Alternately, an arc segment of radiation detectors can be mounted to the rotating gantry to rotate with the x-ray tube.

A control console 16 contains an image reconstruction means 18 for reconstructing an image representation out of signals from the detector array 14. Preferably, the image reconstruction means reconstructs a volumetric image representation from radiation attenuation data taken along a spiral path through the patient A video monitor 20 converts selectable portions of the reconstructed volumetric image representation into a two-dimensional human-readable display. The console 16 also includes appropriate tape and disk recording means for archiving image representations, performing image enhancements, selecting planes, 3D renderings, or color enhancements, and the like. Various scanner control functions such as initiating a scan, selecting among different types of scans, calibrating the system, and the like are also performed at the control console 16.

The x-ray tube B includes an oil filled housing 22 that has an x-ray permeable window directed toward the patient receiving region An evacuated envelope is disposed within the housing holding a rotating anode, such as a 7 inch anode, and a cathode or other electron source. High voltages, on the order of 150 kV and higher applied between the rotating anode and the cathode, cause the generation of x-rays. The x-ray pass through an x-ray permeable window and across the patient receiving region 12. Appropriate x-ray collimators focus the radiation into one or more planar beams which span the examination region 12, as is conventional in the art. A shutter under control from the console 16 selectively gates the beam on and off to control patient dosage. Electrical power from the console is conveyed to electrical slip rings for transferring electrical power and control signals between the console and the x-ray tube, shutter and the like. A high voltage power supply is mounted on the rotating gantry for rotation with the x-ray tube. This permits relatively low voltage to be conveyed across the electrical slip ring and converted to high voltage on the rotating gantry. An oil pump circulates oil from the x-ray tube housing through the annular heat exchanger C.

Figure 2:
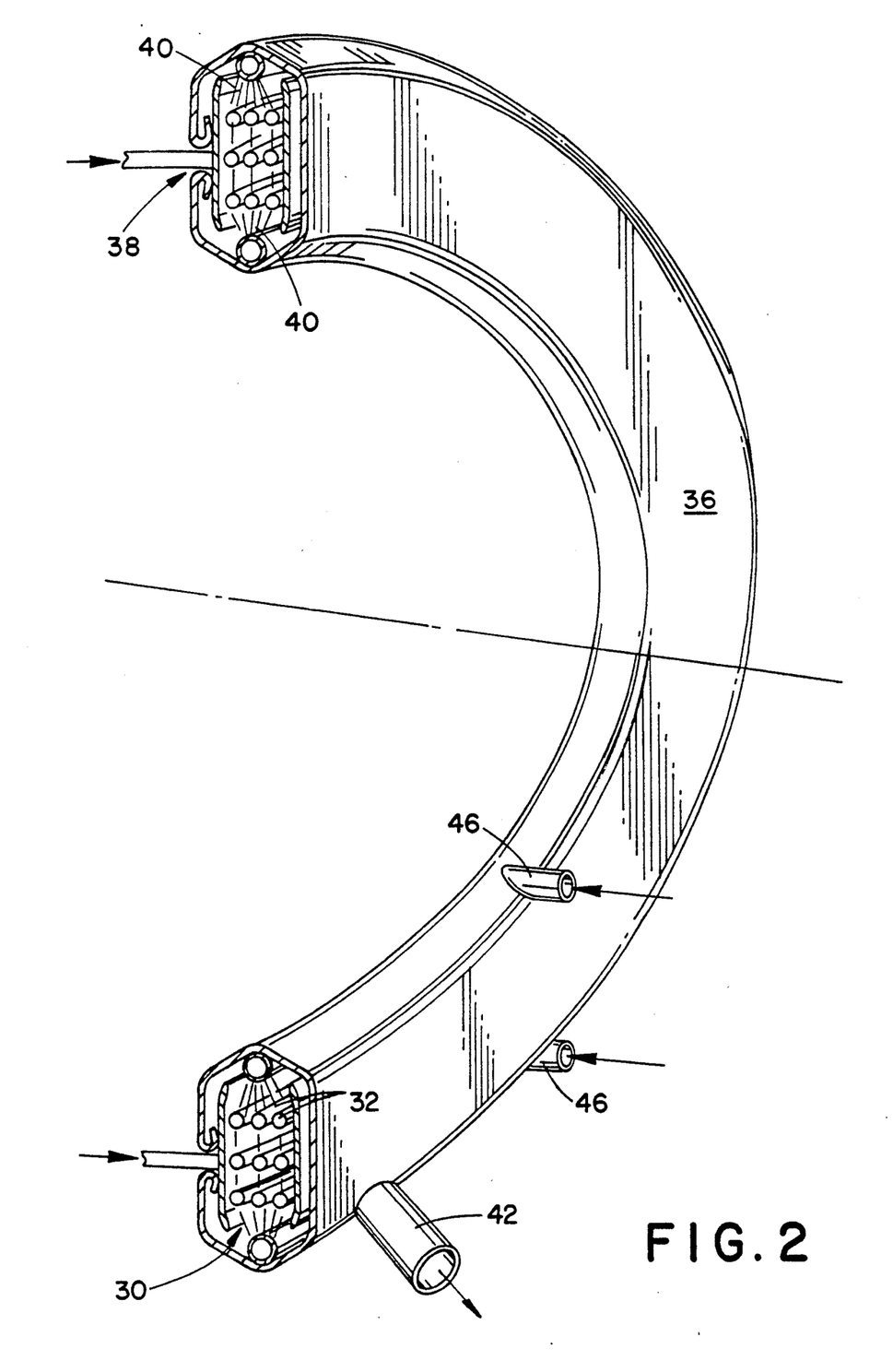
FIG. 2 is a perspective view of the annular heat transfer device of FIG. 1 in partial section.
Figure 3:
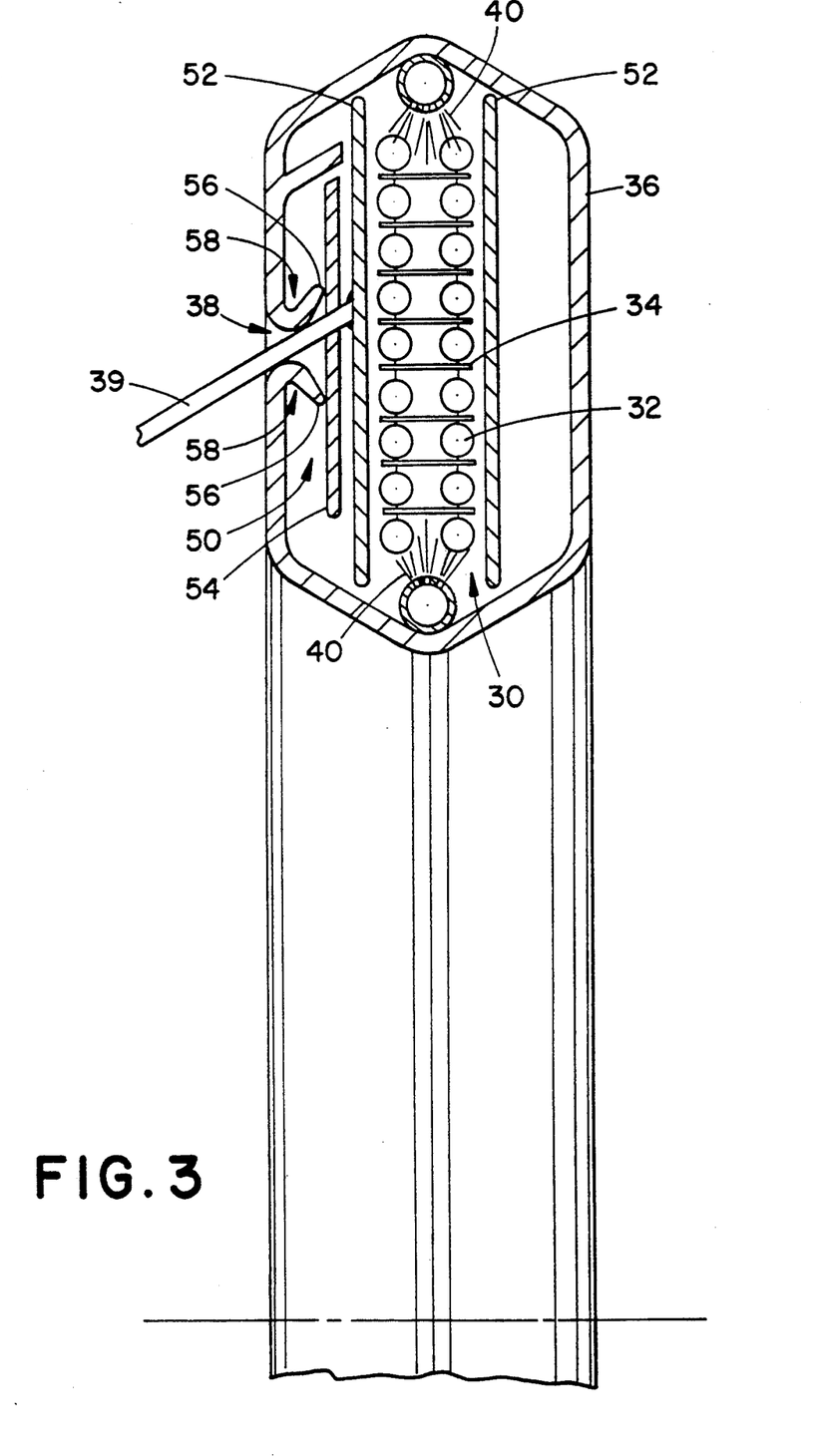
FIG. 3 is a detailed cross-sectional view of the heat transfer device of FIG. 2.

With particular reference to FIGS. 2 and 3, the annular heat exchange means includes an annular rotating radiator 30 which is mounted to the rotating gantry. The radiator includes a plurality of annular loops 32 of tubing that define passages through which the cooling oil of the x-ray tube is circulated. The tubes are interconnected by webs 34 for which increase the heat transfer surface area. The rotating annular radiator 30 is rotatably mounted within a stationary member, particularly an annular tube 36 with an air region in between. The stationary annular tube member defines an annular or circular aperture 38 through which struts 39 and oil circulation passages for the rotating radiator 30 extend.

A plurality of spray jets 40 are mounted within the stationary member. The spray jets spray chilled working fluid, preferably water, on the rotating annular radiator 30. Warmed working fluid which drips or is thrown by centrifugal force off of the rotating radiator is constrained within the annular tube 36 and flows by gravity to a drain 42 at the low point of the stationary member With reference again to FIG. 1, water from the drain 42 is circulated by a pump 44 to the remote heat exchanger D which chills the water to near its freezing point. The chilled water is pumped back to cold water inlets 46 connected with the spray jets 40. In the preferred embodiment, the diameter of the heat exchanger and the water circulation rate are sufficiently high that the water is heated less than about 20° C. during the heat exchange process. By supplying the water near the freezing point, the returned, heated water is around room temperature. Other working fluids or mediums may also be used.

With particular reference to FIG. 3, a leakage inhibiting means 50 is provided for inhibiting the sprayed water from being lost through the annular aperture 38. First, the annular aperture 38 is about mid-way up on a side access of the stationary housing. Second, the rotating radiator 30 includes a pair of side plates 52, which side plates closely approach the spray jets 40 and constrain the spray between the side plates. A sealing baffle 54 is mounted on the supports in a close fitting or rubbing relationship against lips 56 on the stationary housing on either edge of the annular aperture 38. The interaction between the lips and the baffles inhibit water from escaping through annular aperture 38. In order to prevent water which flows to the drain 42 that flows down the side of the stationary housing from entering the annular aperture 38, gutters 58 are defined on either side. Additional means may also be provided for inhibiting the sprayed and draining water from leaving the annular tube 36. The leakage inhibiting means preferably includes a Teflon coating on the struts 39 and other parts that extend through the annular aperture 38 and the side walls of the stationary housing to prevent the working fluid from creeping therealong. The struts 39 also angle radially outward from the rotating gantry to the rotating radiator such that any working fluid that reaches the struts is urged by centrifugal force out along the strut, through the annular aperture 38 and into the annular tube 36. Alternately, the tube 36 can rotate with the radiator Water inlet tubes for the spray nozzles and a siphon drain tube would pass through the annular aperture 38 rather than struts 39. Analogous leaking inhibiting means would be used to prevent the working fluid from leaking through the annular aperture.

Figure 4:
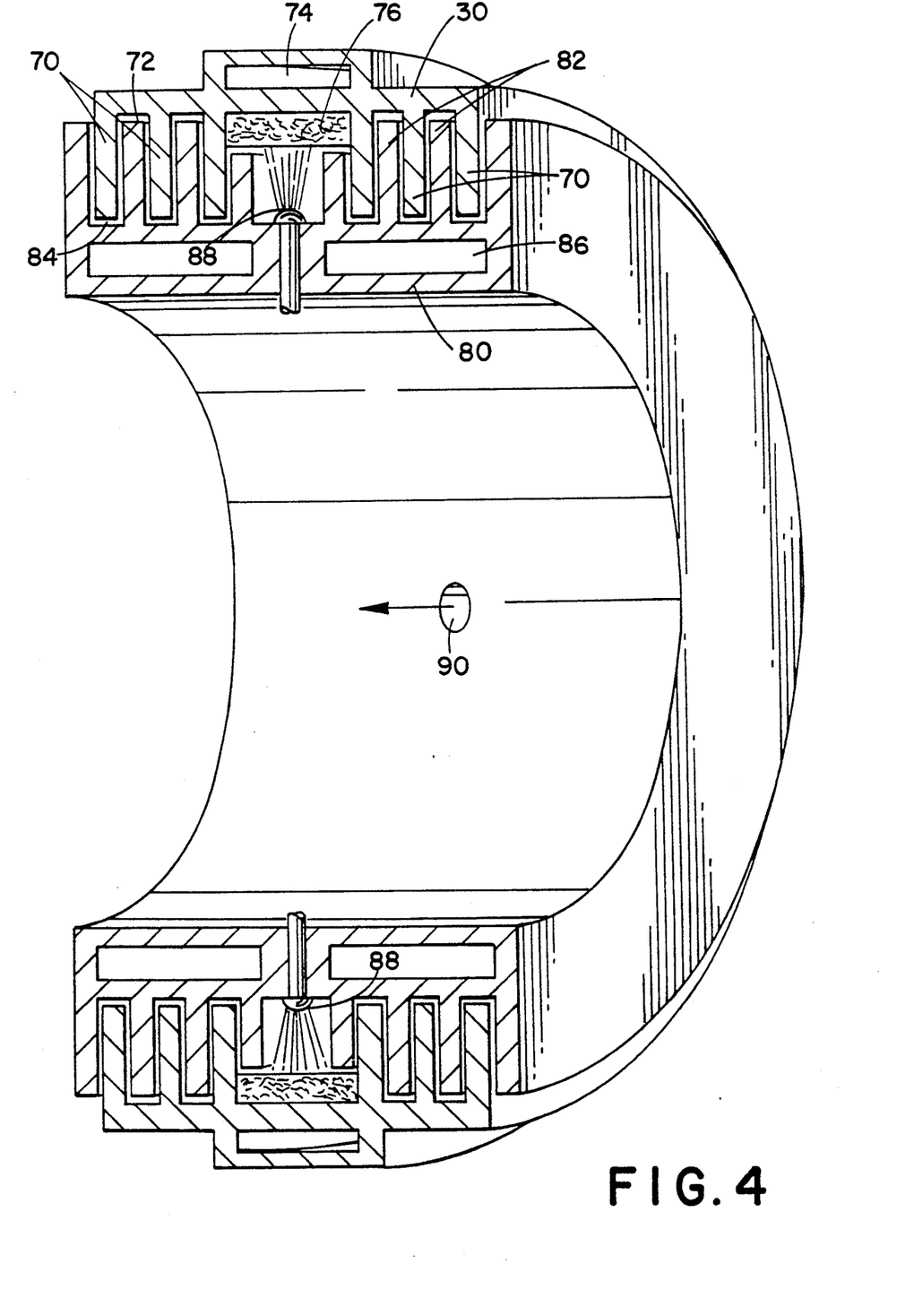
FIG. 4 is a perspective view in partial section of an alternate embodiment of the annular heat transfer mechanism.

With reference to FIG. 4, the rotating radiator 30 defines a series of annular vanes or fins 70 which define annular valleys 72 in between. An oil passage 74 extends along the radiator 30. A wick of porous material 76 is mounted in a central, widened valley of the rotating radiator. The wick may be a felt material, a porous ceramic, or the like. Preferably, the wick is mounted as closely contiguous to the hot oil as possible.

A mating stationary heat exchange member 80 defines a plurality of annular vanes or fins 82 and annular valleys 84. The stationary annular fins are received in the valleys 72 of the rotating radiator and the fins 70 of the rotating heat exchanger member are received in the valleys 84 of the stationary member. These fins and valleys define a tortuous air flow path of relatively narrow dimension such that heat is transferred through the air from the hot rotating fins to the cool stationary fins. Working fluid channels 86 are defined within the stationary member for circulating a working fluid which is also circulated to the remote chiller D. A plurality of spray nozzles 88 are mounted in the stationary member 80 directly opposite the wick 76. The nozzles spray the working fluid on the wick to replace water lost by evaporation as the water absorbs heat energy from the hot oil. One or more exhaust ports 90 are connected with an air exhaust fan for exhausting hot humid air to a remote location outside of the examination room. The exhaust fan pulls air through the tortuous path between the rotating and stationary fins into the region between the wick and the spray nozzles. The humid air is removed sufficiently quick that the air around the wick does not become saturated and reduce water evaporation, hence the evaporative cooling effect. In addition, by increasing this airflow the rate of heat transfer can be increased as needed. Some of the humidity in the air will be condensed on the stationary cold fins with the heat of condensation being absorbed by the working medium. The recondensed liquid flows by gravity towards the lower half of the annular cooling region and drips onto the wick. The spray jets primarily provide peak demand cooling. That is, the spray jets only operate when the x-ray tube is running. At other times, the air may continue to be circulated in order to remove any residual heat in the oil and other equipment, returning it fully to room temperature. The spray jets are then reactivated when the air cooling falls behind.

Figure 5:
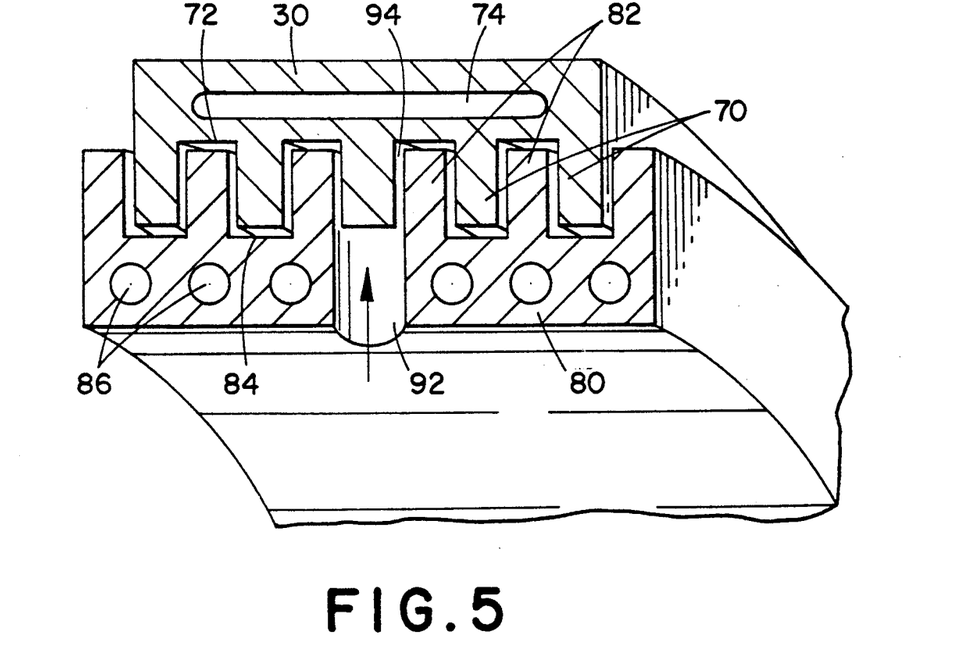
FIG. 5 is a cross-sectional view of another alternate embodiment of the annular heat transfer mechanism; and, FIG. 6 is a cross-sectional view of yet another alternate embodiment of the annular heat transfer device.

With reference to FIG. 5, the rotating radiator 30 again includes a plurality of annular fins or vanes 70 and annular valleys 72. A stationary member 80 includes a plurality of annular fins or vanes 82 which are received in the rotating valleys 72 and a plurality of valleys 84 which receive the rotating fins 70. Working fluid channels 86 circulate a working medium which is returned to the remote cooling site D to be chilled to a low temperature, preferably below 0° C. An air circulating means pumps cold air into a plurality of central ports 92 through the stationary member. The air may be pumped directly through the stationary heat transfer member as illustrated or may follow a tortuous path along cooled surfaces such that the stationary member absorbs heat from the air, cooling it still further. The air is pumped through the tortuous air region 94 between the alternating stationary and rotating fins. The air acts as a transfer medium to absorb heat from the rotating fins and give up heat to the stationary fins. A sufficient number of fins and cooling surfaces are provided that the air emerges at the edges substantially at room temperature. Additional cool stationary fins may be provided, as necessary, to bring the air down to room temperature.

Figure 6:
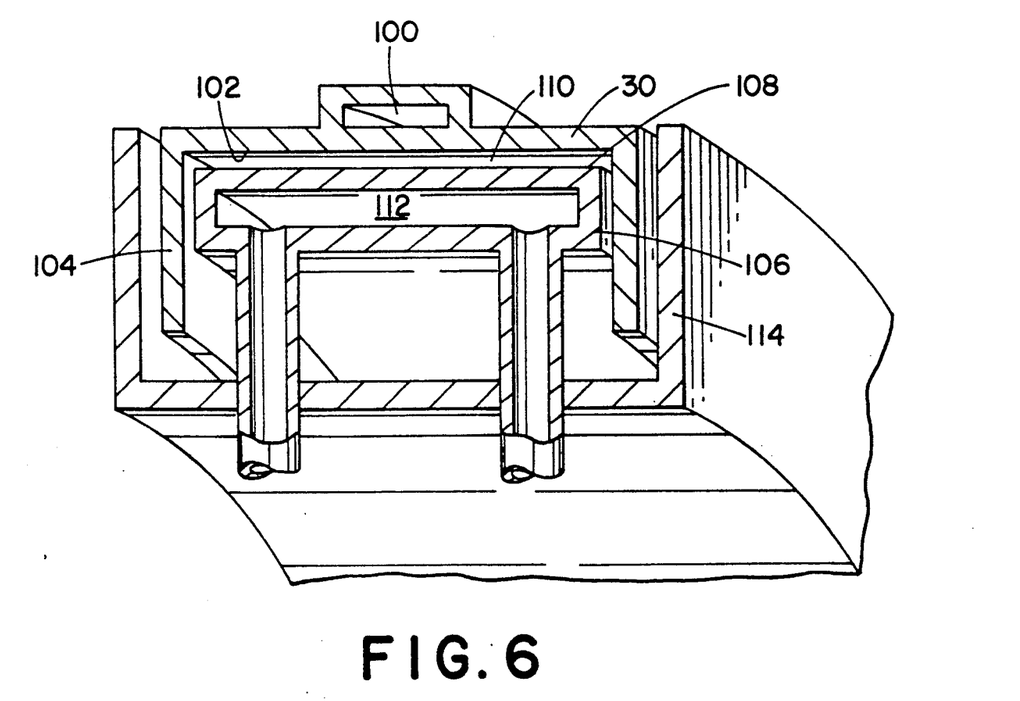

With reference to FIG. 6, the rotating radiator 30 includes a hot oil passage 100 along one surface of a substantially horizontal heat exchange surface Downward depending flanges 104 help prevent fluid loss. A stationary heat exchange member 106 having a stationary horizontal heat exchange surface 108 is mounted opposite the rotating heat exchange surface 102, defining a narrow, annular air region 110 therebetween. Cool working fluid is circulated through passages 112 in the stationary member to the remote cooling means D. The stationary member is connected with an annular shield or gutter means 114 which defines a relatively deep well at least at the low end of the CT scanner. The depth and width of the well at the low end is selected to be significantly larger than the volume of the thin annular air region 110. During rotation, centrifugal force causes the water or other working fluid at the bottom of the gutter 114 to coat the rotating radiator heat exchange surface 102. Sufficient water is provided that the gap 110 is filled. In this manner, the working fluid provides a heat transfer path between the rotating and stationary heat exchange surfaces. When the rotating gantry stops, the water or other working fluid flows by gravity into the low point of the gutter, which, again has sufficient depth to hold the entire volume of working fluid.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A CT scanner comprising:
   a patient receiving region defined within a stationary gantry;
   a fluid cooled x-ray tube mounted on a rotating gantry, the rotating gantry mounted to the stationary gantry for rotation about the patient receiving region, the x-ray tube transmitting a beam of x-rays across the patient receiving region;
   a radiation detection means for detecting radiation which has traversed the patient receiving region;
   an image reconstruction means for reconstructing an electronic image representation from signals generated by the X-ray detection means;
   an annular heat transfer means for transferring heat from the x-ray tube cooling fluid to the stationary gantry, the annular heat transferring means including:
      an annular radiator mounted to the rotating gantry for rotation therewith, the annular radiator means including a passage therethrough through which the x-ray tube cooling fluid is circulated;
      a stationary member disposed adjacent the rotating annular radiator, the stationary member and the rotating radiator defining an air region therebetween;
      a wick portion of porous material mounted to the annular radiator in the air region;
      a means for wetting the wick material with a working fluid that evaporates cooling the x-ray tube cooling fluid with evaporative cooling;
      a remote heat exchange means for circulating a working fluid from the stationary member to a remote location where heat is removed and returning cooled working fluid to the wick material wetting means.

2. The CT scanner as set forth in claim 1 wherein the wick material wetting means includes a plurality of spray nozzles mounted to the stationary member for spraying the working fluid on the rotating annular radiator.

3. The CT scanner as set forth in claim 1 wherein the rotating radiator and the stationary member define a plurality of interleaved annular vanes which define a tortuous air path between and further including a means for circulating air through the tortuous path and past the wick material such that the air (1) transfers heat through the air from the rotating radiator member to the stationary member and (2) removes the evaporated working fluid to prevent the air path from becoming saturated with humidity.

4. A radiographic apparatus comprising:
   a patient receiving region defined within a stationary gantry;
   an oil cooled radiation generator mounted on a rotating gantry, the rotating gantry mounted to the stationary gantry for rotation about the patient receiving region, the radiation generator transmitting a beam of radiation across the patient receiving region;
   an annular heat transfer means for transferring heat from the radiation generator cooling oil to the stationary gantry, the annular heat transferring means including:
      an annular radiator mounted to the rotating gantry for rotation therewith, the annular radiator means including an oil passage therethrough through which the cooling oil is circulated;
      a stationary member disposed adjacent the rotating annular radiator, the stationary member and the rotating radiator defining an air region therebetween;
   a plurality of liquid spray nozzles mounted circumferentially around the stationary member for spraying a liquid working fluid on the rotating annular radiator.

5. A radiographic apparatus comprising:
   a patient receiving region defined within a stationary gantry;
   an oil cooled radiation generator mounted on a rotating gantry, the rotating gantry mounted to the stationary gantry for rotation about the patient receiving region, the radiation source transmitting a beam of radiation across the patient receiving region;
   an annular heat transfer means for transferring heat from the cooling oil to the stationary gantry, the annular heat transferring means including:
      an annular radiator mounted to the rotating gantry for rotation therewith, the annular radiator means including an oil passage therethrough through which the cooling oil is circulated, the rotating radiator including a wick portion of porous material;
      a means for wetting the wick material with a working fluid that evaporates cooling the x-ray tube cooling oil with the evaporative cooling;
      a stationary member disposed adjacent the rotating annular radiator, the stationary member and the rotating radiator defining an air region therebetween.

6. A CT scanner comprising:
   a patient receiving region defined within a stationary gantry;
   a fluid cooled x-ray generator mounted on a rotating gantry, the rotating gantry mounted to the stationary gantry for rotation about the patient receiving region, the x-ray generator transmitting a beam of x-rays across the patient receiving region;
   a radiation detection means for detecting radiation which has traversed the patient receiving region;
   an image reconstruction means for reconstructing an electronic image representation from signals generated by the x-ray detection means;
   an annular heat transfer means for transferring heat from the x-ray generator cooling fluid to the stationary gantry, the annular heat transferring means including:
      an annular radiator mounted to the rotating gantry for rotation therewith, the annular radiator means including a passage therethrough through which the x-ray generator cooling fluid is circulated;
      an annular tube which substantially surrounds the rotating annular radiator, the annular tube and the rotating radiator defining an air region therebetween, and annular tube defining an annular aperture through which supports for supporting the rotating radiator on the rotating gantry extend and through which cooling fluid channels for transferring x-ray generator cooling fluid between the x-ray generator and the radiator extend;

spray nozzles disposed on the interior of the annular tube for spraying working fluid on the rotating radiator; and leakage inhibiting means for inhibiting the sprayed working fluid from exiting through the annular aperture.

7. The CT scanner as set forth in claim 6 wherein the leakage inhibiting means includes at least one of:

means for directing the sprayed working fluid onto the rotating radiator and away from the annular aperture, a lip arrangement on either side of the annular aperture and a shielding baffle which rotates with the rotating radiator, gutters adjacent either edge of the annular aperture, a Teflon or other anti-wetting coating on the support members for supporting the rotating radiator and the baffles to prevent the working fluid from creeping along the support members, and angling the support members radially inward from the radiator such that centrifugal force urges any working fluid which reaches the support members toward the radiator and away from the rotating gantry.

8. The CT scanner as set forth in claim 6 further including a drain outlet at a bottom of the annular tube, the drain outlet being connected with a remote heat exchange means.

9. A CT scanner comprising:

a patient receiving region defined within a stationary gantry;

a fluid cooled x-ray tube mounted on a rotating gantry, the rotating gantry mounted to the stationary gantry for rotation about the patient receiving region, the x-ray tube transmitting a beam of x-rays across the patient receiving region;

a radiation detection means for detecting radiation which has traversed the patient receiving region;

an image reconstruction means for reconstructing an electronic image representation from signals generated by the x-ray detection means;

an annular heat transfer means for transferring heat from the x-ray tube cooling fluid to the stationary gantry, the annular heat transferring means including:

an annular radiator mounted to the rotating gantry for rotation therewith, the annular radiator means including a passage therethrough through which the x-ray tube cooling fluid is circulated;

a stationary member disposed adjacent the rotating annular radiator, the stationary member and the rotating radiator defining an air region therebetween;

a remote heat exchange means for circulating a working fluid from the stationary member to a remote location where heat is removed and returning cooled working fluid to the stationary member, the working fluid including water.

10. The CT scanner as set forth in claim 9 further including a spray nozzle means disposed around the stationary member for spraying water on at least a portion of the rotating radiator.

11. A method of transferring heat from an x-ray tube on a rotating gantry to a stationary gantry, the method comprising:

circulating a cooling fluid from the x-ray tube through internal passages of a rotating, annular radiator;

spraying a working fluid on a wick material connected with the rotating radiator;

evaporating the working fluid from the wick material such that the rotating radiator is cooled by evaporative cooling; and, removing the evaporated vapor such that air does not become saturated and evaporative cooling continues.

12. A CT scanner comprising:

a patient receiving region defined within a stationary gantry;

a fluid cooled x-ray tube mounted on a rotating gantry, the rotating gantry mounted to the stationary gantry for rotation about the patient receiving region, the x-ray tube transmitting a beam of x-rays across the patient receiving region;

a radiation detection means for detecting radiation which has traversed the patient receiving region;

an image reconstruction means for reconstructing an electronic image representation from signals generated by the x-ray detection means;

an annular heat transfer means for transferring heat from the x-ray tube cooling fluid to the stationary gantry, the annular heat transferring means including:

an annular radiator mounted to the rotating gantry for rotation therewith, the annular radiator means including a passage therethrough through which the x-ray tube cooling fluid is circulated;

a stationary member disposed adjacent the rotating annular radiator, the stationary member and the rotating radiator defining an air region therebetween;

a gutter means substantially surrounding the rotating radiator; and a means for distributing a working fluid into contact with the rotating radiator and catching the working fluid with the gutter means;

a remote heat exchange means for circulating the working fluid from the gutter means to a remote location where heat is removed and returning cooled working fluid to the working fluid distributing means.

13. The CT scanner as set forth in claim 12 wherein the water distributing means includes spray nozzles mounted within the gutter means for spraying the rotating radiator means, the gutter means having a drain connected with the remote heat exchange means for recirculating the working fluid.

14. The CT scanner as set forth in claim 12 further including a porous wick means connected with the rotating radiator and wherein the water distribution means wets the porous wick means.

15. A CT scanner comprising:

a patient receiving region defined within a stationary gantry;

a fluid cooled x-ray generator mounted on a rotating gantry, the rotating gantry mounted to the stationary gantry for rotation about the patient receiving region, the x-ray generator transmitting a beam of x-rays across the patient receiving region;

a radiation detection means for detecting radiation which has traversed the patient receiving region;

an image reconstruction means for reconstructing an electronic image representation from signals generated by the x-ray detection means;

an annular heat transfer means for transferring heat from the x-ray tube cooling fluid to the stationary gantry, the annular heat transferring means including:

an annular radiator mounted to the rotating gantry for rotation therewith, the annular radiator means including a passage therethrough through which the x-ray generator cooling fluid is circulated;

a stationary member disposed adjacent the rotating annular radiator, the stationary member and the rotating radiator defining an air region therebetween, the stationary member including an annular, working fluid retaining gutter which extends peripherally around the rotating radiator for catching a working fluid at least in a lower portion thereof;

a remote heat exchange means for circulating the working fluid from the fluid retaining gutter to a remote location where heat is removed and returning cooled working fluid to the stationary member.

16. The CT scanner as set forth in claim 15 wherein the rotating radiator means includes a generally flat, horizontal heat exchange surface and wherein the stationary member further includes a generally flat, horizontal heat exchange surface disposed across the air region from the rotating heat exchange surface;

the working fluid from the remote heat exchange means being circulated through the stationary member to cool the stationary heat exchange surface;

working fluid disposed in the gutter such that when the rotating gantry rotates, working fluid is thrown by centrifugal force into the air region between the rotating and stationary heat exchange surfaces such that the working fluid functions as a heat exchange medium transferring heat from the rotating heat exchange surface to the stationary heat exchange surface.

17. A radiographic apparatus comprising:

a patient receiving region defined within a stationary gantry;

a oil cooled x-ray tube mounted on a rotating gantry, the rotating gantry mounted to the stationary gantry for rotation about the patient receiving region, the x-ray tube transmitting a beam of x-rays across the patient receiving region;

an annular heat transfer means for transferring heat from the x-ray tube cooling oil to the stationary gantry, the annular heat transferring means including:

an annular radiator mounted to the rotating gantry for rotation therewith, the annular radiator means including an oil passage therethrough through which the x-ray tube cooling oil is circulated;

a stationary member disposed adjacent the rotating annular radiator, the stationary member and the rotating radiator defining a heat transfer region therebetween, the stationary member including an annular, working fluid retaining gutter means which extends peripherally around the rotating radiator for catching a working fluid;

a working fluid introducing means for introducing a working fluid into the heat transfer region.

18. The apparatus as set forth in claim 17 further including a remote heat exchange means for circulating a working fluid from the gutter means to a remote location where heat is removed and returning cooled working fluid to the working fluid introducing means, and wherein the working fluid introducing means includes a spray nozzle means mounted to the stationary member for spraying the working fluid on the rotating annular radiator.

19. The apparatus as set forth in claim 18 wherein the rotating radiator and the stationary member define a plurality of interleaved annular fins which define a tortuous air path therebetween and further including a means for circulating air through the tortuous path such that the air transfers heat through the air from the rotating radiator member to the stationary member.

20. The apparatus as set forth in claim 18 wherein the gutter means includes an annular tube which surrounds the rotating radiator, the annular tube defining an annular aperture through which supports for supporting the rotating radiator on the rotating gantry extend and through which cooling fluid channels for transferring the x-ray tube cooling oil between the x-ray tube and the rotating radiator extend.

21. The apparatus as set forth in claim 20 further including a leakage inhibiting means for inhibiting the sprayed working fluid from exiting through the annular aperture, the water leakage inhibiting means including at least one of: a means for directing the sprayed working fluid onto the rotating radiator and away from the annular aperture, a lip arrangement on either side of the annular aperture and a shielding baffle which rotates with the rotating radiator, rolled gutters adjacent either edge of the annular aperture, an anti-wetting coating on the support members for supporting the rotating radiator to prevent water from creeping along the support members, and angling the support members radially outward from the rotating gantry to the rotating radiator such that centrifugal force urges any working fluid which reaches the support members toward the rotating radiator and away from the rotating gantry.

22. The apparatus as set forth in claim 21 further including a drain outlet at a bottom of the annular tubing, the drain outlet being connected with the remote heat exchange means.

23. The apparatus as set forth in claim 17 wherein:

the rotating radiator means includes a generally flat, horizontal heat exchange surface and wherein the stationary member further includes a generally flat, horizontal heat exchange surface disposed across the heat transfer region from the rotating heat exchange surface;

the working fluid from a remote heat exchange means being circulated through the stationary member to cool the stationary heat exchange surface;

working fluid from the heat exchange region centrifugal force into the heat exchange region between the rotating and stationary heat exchange surfaces such that the working fluid functions as a heat exchange medium transferring heat from the rotating heat exchange surface to the stationary heat exchange surface.

24. The CT scanner comprising:

a patient receiving region defined within a stationary gantry;

a fluid cooled x-ray tube mounted on a rotating gantry, the rotating gantry mounted to the stationary gantry for rotation about the patient receiving region, the x-ray tube transmitting a beam of x-rays across the patient receiving region;

a radiation detection means for detecting radiation which has traversed the patient receiving region;

an image reconstruction means for reconstructing an electronic image representation from signals generated by the x-ray detection means;

an annular heat transfer means for transferring heat from the x-ray tube cooling fluid to the stationary gantry, the annular heat transferring means including:

an annular radiator mounted to the rotating gantry for rotation therewith, the annular radiator means including a passage therethrough through which the x-ray tube cooling fluid is circulated, the rotating radiator including a plurality of annular fins which define valleys therebetween;

a stationary member disposed adjacent the rotating annular radiator, the stationary member including a plurality of annular fins which define valleys therebetween, the stationary fins extending into the valleys between the rotating fins and the rotating fins extending into the valleys between the stationary fins, a region being defined between the rotating and stationary fins, working fluid circulating apertures extending through the stationary member into a generally axially central valley thereof for circulating a working fluid;

a means for causing the working fluid to flow axially over the stationary and rotating fins through the region defined therebetween between circumferential edges of the stationary member and the apertures.

25. A method of transferring heat from an x-ray tube on a rotating gantry to a stationary gantry, the method comprising:

circulating a cooling fluid from the x-ray tube through internal passages of a rotating, annular radiator;

spraying a cooling liquid working fluid which includes water on the rotating radiator to absorb heat;

collecting the heated working fluid with the stationary gantry.

26. The method as set forth in claim 25 further including cooling the collected working fluid at a remote location, and returning the cooled working fluid for spraying on the rotating radiator.

27. The method as set forth in claim 25 wherein the x-ray tube and rotating gantry are part of a CT scanner.

* * * * *